United States Patent [19]
Becker et al.

[11] Patent Number: 4,952,143
[45] Date of Patent: Aug. 28, 1990

[54] DENTAL BLEACHING INSTRUMENT

[76] Inventors: William J. Becker, 3 Twin Brooks Rd., New Milford, Conn. 06776; Kenneth S. Magid, 3 Finch La., Bedford, N.Y. 10506

[21] Appl. No.: 195,086
[22] Filed: May 17, 1988
[51] Int. Cl.$^5$ .............................................. A61C 3/00
[52] U.S. Cl. .................................... 433/32; 433/215; 433/229
[58] Field of Search .............. 433/32, 215, 216, 217.1, 433/229

[56] References Cited

U.S. PATENT DOCUMENTS

4,597,712  7/1988  Demand ................................. 433/32
4,661,070  4/1987  Friedman ............................ 433/229

Primary Examiner—John J. Wilson
Attorney, Agent, or Firm—Andrew S. Langsam

[57] ABSTRACT

A dental bleaching instrument with a source for generating heat. A temperature sensor can be distanced from the heat generator for determining the heat proximal to the teeth. That more accurately reflects the temperature of the heat actually reaching the tooth surface. The light used for bleaching the teeth provides, originally, IR, optically visible light and UV wavelengths. All UV and optically visible light is filtered except for a narrow band of optically visible light to facilitate aiming. Also, the heat source of the device is physically separable from the power and control mechanism yet electrically connected thereto, to facilitate alignment and location of the light with respect to the patient.

9 Claims, 3 Drawing Sheets

DENTAL BLEACHING INSTRUMENT

BACKGROUND OF THE INVENTION

The present invention relates to a dental bleaching instrument with a heat generating mechanism which is useful in bleaching, primarily for cosmetic purposes, dental tooth structure. The necessity or desirability of bleaching or whitening teeth is due to the teeth either having undergone root canal therapy and have thus become darkened or, the teeth have been traumatized by an accident or, even, where the patient simply desires whiter looking teeth. The present invention relates to a dental bleaching instrument which serves, by directing heat, to activate the chemical reaction of a peroxide-like solution or any other bleaching solution which is either first applied directly to the tooth structure which is sought to be bleached as, for example, by brushing or, alternatively, the bleaching solution is passed through a predrilled hole in the tooth structure (in the case where root canal-type therapy has been previously performed). The term "peroxide solution" is frequently used herein, yet, it should be understood that the present invention is intended to function with any bleaching substance or solution, if "curing" or activating is performed by the application of heat. Alternatively, the teeth to be bleached are wrapped with gauze and the gauze is soaked with the bleaching solution. In any event, however, a peroxide solution is applied to either an individual tooth or multiple teeth and, in order to achieve the desired bleaching effect, it is necessary for heat to be applied to the bleaching solution on the teeth for a minimum period of time at a minimum temperature. The dental bleaching instrument provides a means for precisely controlling and monitoring the heat provided, so as to obtain desired uniform and controlled bleaching results.

The present invention also provides a dental bleaching instrument which enables the dentist to perform the teeth-bleaching procedure without having the wavelengths ordinarily emitted by the heat generating means negatively impact on either patient or dentist or dental technician and, in addition, provides a more accurate controlling of the entire dental procedure so that discomfort to the patient is minimized along with its attendant anxiety and, indeed, the time for the patient to be located within the dentist's chair is minimized, a benefit to both dentist and patient. The present invention thus relates to a dental bleaching instrument having a temperature sensing and controlling mechanism, a wavelength filtering means and an adjustability for positioning and directing, all of which maximize the dental bleaching procedure.

DESCRIPTION OF THE PRIOR ART

The basic dental procedure of bleaching patient's teeth for either cosmetic purposes where the patient simply wants brighter or whiter looking teeth or, alternatively, where the color of the tooth structure has been damaged by an accident or root canal therapy, has been in existence for some time. A bleaching solution, known in the dental trade as "superoxol," is a peroxide solution and is necessarily activated on the patient's tooth structure by the application of a minimum amount of heat at a predetermined minimum temperature for a minimum duration of time. Prior to the present invention, however, there did not exist any mechanism for controlling, precisely, the quantity of heat supplied to the tooth structure sought to be bleached nor was a mechanism present for precisely controlling the light and heat source so that heat is provided to the tooth structure at a precisely controlled temperature.

U.S. Pat. No. 4,661,070 to Freidman relates to a method for bleaching discolored teeth. According to that reference, a method for treating discolored teeth is provided by first applying a concentrated solution of peroxide to the tooth surface and then a beam of optical energy is focused onto the tooth structure. The beam of optical energy contains ultra-violet waves in a defined wavelength range in combination with infra-red waves also in a defined wavelength range. The IR and UV rays, according to the reference, synergistically activate the peroxide solution. The reference teaches simultaneously suppressing a range of wavelengths from reaching the tooth or teeth to be treated while allowing the IR and UV wavelengths to be directed onto the tooth structure. This reference, however, suffers from the disadvantage in that it specifically requires and, indeed, provides for the emission and transmission of ultra-violet wavelengths from the beam of light onto tooth structure and surroundings. Studies, however, have consistently shown that ultra-violet rays have a negative effect upon dentists or dental technicians working proximal to such light and, indeed, it is quite possible that the long term negative effects of working closely adjacent to this high-tensity, ultra-violet wavelengths have not yet fully been appreciated. For this reason, inter alia, the present invention seeks to specifically block substantially all of the ultra-violet wavelengths from reaching the patient, dentist, etc. while the Friedman reference specifically requires and provides transmission of UV light to both the tooth structure and, in addition, by reflection and refraction to the patient, dentist and dental technician.

Also in existence, prior to the present invention, is a soldering-type iron whose tip temperature was desirably controlled and varied. The heated tip physically contacts, via two alternate tip shapes, the tooth structure which was sought to be heated to a temperature such that the bleaching solution, applied therto, would be sufficiently activated for proper bleaching. The tip of this soldering-type iron dental instrument would, in one configuration, be tooth shaped, for physically contacting the individual tooth to be bleached or, alternatively, in intra coronal tooth bleaching, the soldering-type iron would provide a mere point of contact, which would be inserted into a pre-drilled hole of the tooth to be treated. In either event, however, this soldering-type iron and the method of bleaching teeth by its use, suffer from a significant disadvantage in that it is only applicable to individual teeth bleaching at a time and, therefore, suffers from the significant disadvantage in that multiple teeth if desirably bleached, require an extremely long time for the patient to be in the dental chair which, clearly, creates a problem for both patient and dentist.

Obviously, it is highly desirable to bleach, simultaneously, multiple teeth, not only from a point of view of minimizing procedure time but, in addition, from the point of view of tooth color uniformity. It is highly desirable to apply the activating energy to multiple teeth at the same time so that uniform conditions are maintaned, as much as possible, such that the ultimately achieved color of the bleached teeth, as near as possible, are the same. Also, with the soldering type of iron, about one-half hour of physical contact, whether constant or intermittent with periods of rest, is required between the heated tip of the soldering-type iron and the tooth structure being treated. This, too, is a disadvantage from the point of view of requiring the dentist or dental technician to manually hold the tip of the device on the tooth structure and, in addition, as previously mentioned, requires the patient to be seated in the dental chair for a long period of time for multiple tooth bleaching.

The Friedman reference, discussed above, shows a device quite similar, in overall configuration, to a dental curing light which has been used for curing dental restorative materials. The cross-section of the wavelength guide of the Friedman device is, according to the specification of Friedman, either tooth-shaped or circular but, in any event, it is certainly contemplated by Friedman that one individual tooth, at a time, be treated. Here, again, it is then necessary for the dentist to physically hold the light gun for a total of about one-half hour, whether that holding time is constant or, even, intermittent, for each tooth sought to be treated. Clearly, when multiple teeth, at a single sitting are desirably bleached, the overall time for the bleaching technique is extremely long both from the patient's point of view and the dentist's point of view. Also, as previously mentioned, it is often desired to have substantial uniformity in tooth to tooth color and thus it is clearly desirable to do as many teeth as can be practically performed at the same time when substantially the same operating conditions. A device such as the Friedman device which is capable of activating the bleaching solution for only individual teeth, at a time, suffers from serious disadvantages.

Also in existance in the prior art, with respect to dental bleaching procedures, is a spot light system which provides a heat lamp. This type of light system, however, produces visible white light, with attendant glare, which is clearly undesirable from the patient's point of view. Ordinarily, to combat the high glare of the white light, the patient is provided with protective glasses but, this, too, has obvious disadvantages. These spot light heat lamps, have in the past, been provided with a variable heat-intensity controlling mechanism in the nature of a rheostat control, but there has, prior to the present invention, been no attempt at controlling the temperature, precisely, and correlating the heat supplied to a time of application so as to provide the dentist or dental technician with an accurate mechanism for bleaching teeth in a controlled manner. The spot light heat lamp system does, however, allow for the simultaneous bleaching of multiple teeth at a time because of the relatively wide spread of light emitted by this type of lamp. This type of system, however, does not provide any mechanism for sensing the temperature of the heat actually reaching proximal to the treated tooth surface itself and, this too, is a serious disadvantage. Furthermore, the heat lamp is generally located at about 12-14 inches away from the tooth structure sought to be bleached and, therefore, localized factors, for example, ambient temperature, air flow etc., can effect the temperature actually being directed to the tooth structure or surface being bleached. Also, as the heat lamp ages the actual temperature emitted by the lamp, for a particular rheostat setting, generally decreases and this, too, provides an unknown or not controlled variable which negatively impacts on the precision and accuracy of the bleaching procedure. Therefore, it is highly desirable to provide a temperature sensing mechanism for detecting the actual temperature either emitted by the heat source or, alternatively, the temperature which actually reaches the dental tooth structure. In this manner, as will be more fully explained hereinafter, the dentist has precise control over the bleaching procedure and can achieve superior desired results.

It has also been found that the electronics, namely, the transformer, during heating up of the heating source during a bleaching procedure, causes the actual temperature of the lamp generally to change from the desired temperature setting of the rheostat and, thus, the dentist is again not in precise control of the actual temperature being emitted by the heat source nor is he aware of the actual temperature of the heat which reaches the dental or tooth structure.

The light of the spot light system, referred to above, basically requires a substantial perpendicularity between the beam of light and the tooth surface sought to be bleached. The spot light and its side supports must be located on a flat, parallel to the ground, support; often a tray or side table is used and the dentist frequently "jury rigs" the side trays to accommodate the spot light system. Where a tray or flat support is available, however, it is necessarily maintained parallel to the ground and, therefore, the patient must be located in a relatively uncomfortable position, i.e., with his back substantially perpendicular to the ground so that the light beam is perpendicularly impacted onto the tooth structure. Clearly, in a dental office, where patient anxiety is certainly a factor, it is far more pleasurable for the patient to be reclining during the dental bleaching procedure, as is commonly done by modern dental chairs then sitting upright and, therefore, the use of the side trays, as a support surface for the light is not a patient-friendly solution. Furthermore, with the patient in a fully upright position in the dental chair, which provides the perpendicularity required between the heat source and the tooth structure sought to be bleached, it is extremely difficult for the dentist to periodically, as required, apply the bleaching solution to the dental tooth structure. Here, again, where the patient is reclining in the dental chair, it is far easier for the dentist or dental technician to apply the bleaching solution to the teeth or tooth structure sought to be bleached, so long as the bleaching lamp can be supported so that the light beam impacts perpendicularly onto the tooth structure.

The present invention, as will be explained hereinafter, solves the disadvantages of the prior art and represents significant advantages in dental bleaching procedures. Dental bleaching is now becoming extremely popular for merely cosmetic purposes, when the patient desires merely whiter teeth, in general, and, in addition, where it is necessary to bleach individual teeth that have undergone root canal therapy or where the tooth structure has become discolored due to trauma.

SUMMARY OF THE INVENTION

The present invention relates to a dental bleaching instrument which is capable of activating a bleaching solution, whether applied to an individual tooth or to several teeth, for bleaching all at the same time.

According to the invention, a heat source, preferably in the form of a halogen quartz-type reflector-type bulb, is maintained in a cylindrical casing or housing such that the light and energy wavelengths emitted thereby are first focused through a filter. In one embodiment of the present invention, the filter serves to block both the ultra-violet rays and substantially all of the visible white light. In the preferred embodiment, however, of the present invention, some optically visible light, in a narrow wavelength range is allowed to be transmitted to the patient so that the dentist can more accurately aim and focus the heat directly onto the patient's tooth structure sought to be bleached. The bulb housing is cooled by a small fan housed therein and the bulb, along with the fan, is electrically connected to a control console or casing.

The control casing, in the preferred embodiment, is provided with a three positional mode selecting switch which serves to allow the selection of power to drive either one of the two heat sources selected (again, depending upon the number of teeth being treated) or, alternatively, causes the power to be completely shut off from the heat sources. In addition, the control casing is provided with an incrementally adjustable temperature selector switch so that the dentist can select the desired temperature of heat application to the tooth structure sought to be bleached.

According to the preferred embodiment of the invention, as will be explained hereinafter, a series of LEDs are provided which display and thus indicate the actual temperature, as sensed, of the heat generated by the heat source. Also, according to the present invention, the actual temperature of heat sensed is either the temperature immediately proximal to the light source employed or, alternatively, the thermocouple which senses the temperature can be remotely located proximal to the mouth of the patient and quite close to the actual tooth being treated. In the preferred embodiment of the present invention where the heat sensor is located closely adjacent to the patient's mouth, the thermocouple is housed within a material mass having substantially identical thermal properties to ordinary tooth structure and the thermocouple, in its material mass housing, is located and supported by the rubber-like dam (which is inserted into the patient's mouth and supported by his teeth duuring the bleaching procedure). In this manner, the actual temperature of the heat reching the patient's teeth is sensed by the thermocouple and, by suitable electrical means, preferably hard wiring, the temperature so sensed is serially displayed on the LED lights. In an alternate embodiment of the present invention, the temperature actually sensed is electrically fed back to the controlling mechanism for the heat of the light bulb such that the actual temperature reaching the patient's treated tooth structure is continuously adjusted to the pre-selected and desired temperature of the bleaching procedure, as originally set by the dentist.

It is another aspect of the present invention to provide substantial positional adjustability to the bleaching light such that substantial perpendicularity is achieved between the beam of the bleachihng light and the tooth surfaces, while allowing the patient to recline in the dental chair. This, at the same time, allows the dentist ease of access to the patient's mouth for application of bleaching solution, as required.

According to the invention, the multiple or wide angle tooth bleaching housing is provided with a ball and socket adjustment mechanism connected to the rear of the control or console casing. A mechanical arrangement, preferably, a dove-tail and mating slot are employed for the connection. The ball and socket serve to enable the proper positioning and aiming of the front face of the heat lamp such that the emitted beam is substantially perpendicular to the patient's tooth structure which is sought to be bleached. In this manner, by providing significant adjustability to the positioning of the heat-providing light bulb, the patient can be fully reclined, in a comfortable position and, in addition, the dentist can easily apply the bleaching solution to the patient's mouth, without discomfort. In addition, for even more ease of positioning and to enable the patient to be even more fully reclined in a comfortable position in the dental chair, the dove-tail portion of the bulb housing can be physically removed from the control casing, merely by sliding it rearwardly with respect to the casing, and the dove-tail can then be inserted into a similar, matingly configured receiving slot of a separate clamp member which has previously been secured to either of the handles of the overhead operAtory light located in the dentist office. These lights which are available in substantially all dental offices are counterbalanced, quite precisely, and enable the dentist to precisely align the beam of light so that it strikes perpendicularly onto the tooth structure sought to be bleached.

As previosuly mentioned, it is an object of the present invention to provide a temperature sensing mechanism. In one embodiment of the invention, the temperature sensor is located immediately adjacent and proximal to the light bulb of the bleaching head. In this manner, the thermocouple will sense the actual temperature of the bulb and provide a display read-out of that temperature to the dentist. Since, as previously mentioned, the temperature of the bulb varies over the life of the bulb as well as with the heat generated within the control casing, during warm-up and use, it is highly desirable to have knowledge of the actual temperature of the heat generated by the bleaching head during the bleaching procedure. If the heat of the bulb drops below a predetermined minimum then the dentist can simply adjust the desired temperature so that the actual emitted heat reaches the desired temperature. Alternatively, if the actual temperature of the heat generated by the bleaching head increases over the selected and desired temperature, as displayed on the control panel, then the dentist can manually drop the selected temperature so that the actual temperature of the heat is close to the original desired temperature. It is an aspect of the invention to have an electrical feedback such that the instrument constantly senses the actual temperature and adjusts the power of the bulb so that the actual temperature of the generated heat is equal to the desired temperature.

In another embodiment of the invention, the thermocouple is located proximal to the patient's mouth. The thermocouple senses the actual temperature of the heat generated by the bleaching head at a position closely adjacent to the teeth of the patient which are being bleached. Here, again, this is a desirable object and provides the dentist with an accurate temperature indication so that the bleaching procedure can be more accurately monitored and controlled. In this embodiment, in addition, it is contemplated that the thermocouple be embedded into a material mass having the thermal properties substantially identical to the tooth structure being bleached. In this manner, the dentist will have a true indication of the approximate surface temperature of the actual tooth or teeth being bleached by the instrument. This, too, can only facilitate the bleaching procedure and the providing of the desired cosmetic result.

In the electrical feedback embodiment of the invention, it is contemplated that the temperature sensing mechanism, preferably, as mentioned, a thermocouple be electrically connected to the power control of the bulb so that the actual temperature of the heat provided is constantly monitored and the power to the bulb is electrically adjusted so that it closely equals the selected temperature. Thus, if the actually sensed temperature raises a predetermined minimum amount above the selected temperature then power is reduced to the bulb so that the actual temeprature drops into the desired and selected temperature range. Alternatively, if the actual temperature, as sensed by the temperature sensing means, i.e., the thermocouple, drops a predetermined minimum amount below the selected and desired temperature then power is increased to the bulb to increase the heat generated thereby until the actual heat sensed by the thermocouple is substantially equal to the preselected and desired temperature.

It is yet another aspect of the present invention that a timer mechanism can be electrically connected to the bleaching light so that the bleaching procedure is, again, closely monitored in terms of time and temperature.

DETAILED DESCRIPTION OF THE DRAWINGS AND THE PREFERRED EMBODIMENT

Figure 1:
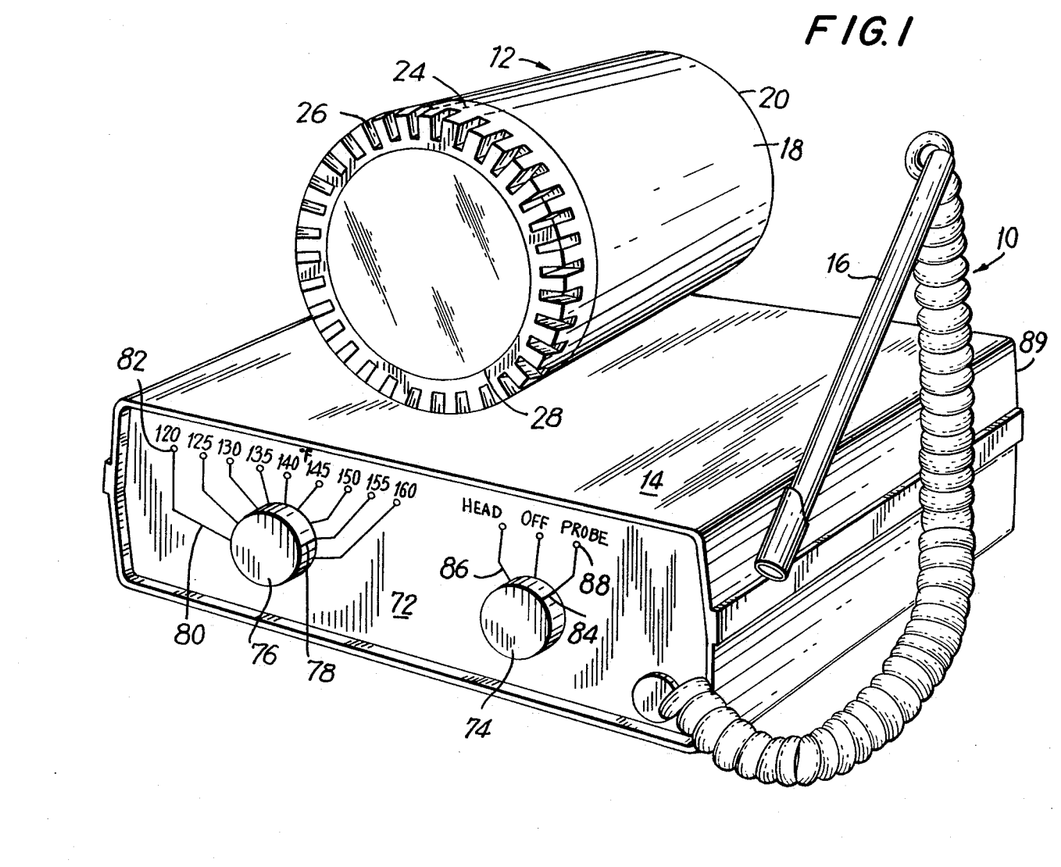
FIG. 1 is a perspective view of the preferred embodiment of the dental bleaching instrument.
Figure 2:
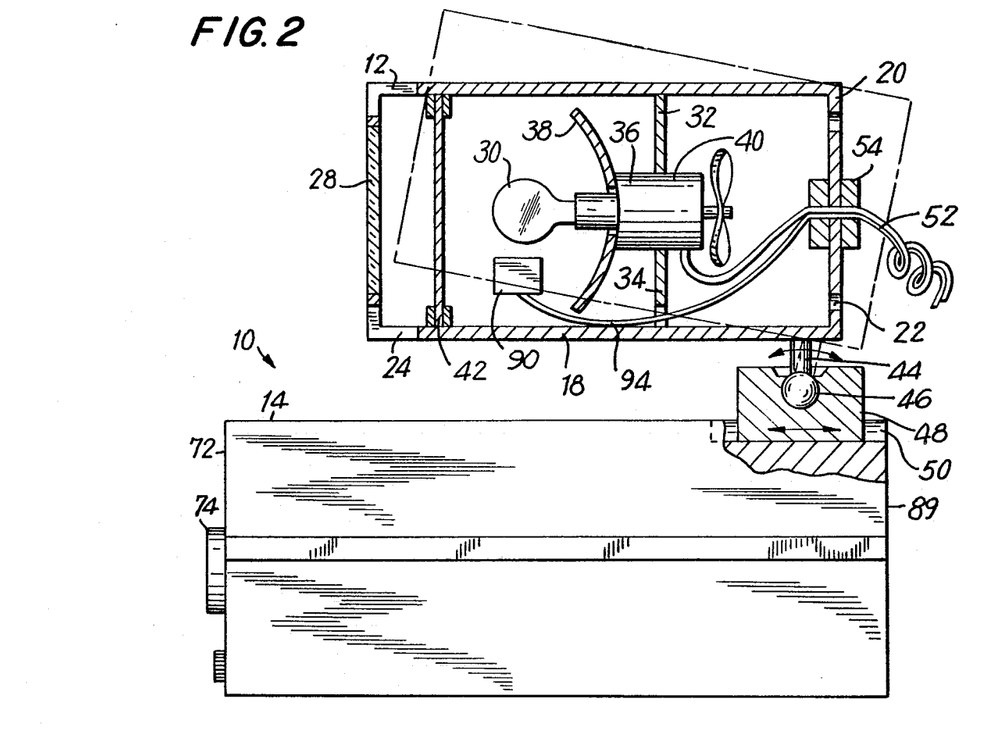
FIG. 2 is a cross-sectional view of the dental bleaching instrument shown in FIG. 1 and taken along lines 2—2 of FIG. 1.

As best shown in FIGS. 1 and 2, the dental bleaching instrument, generally indicated as 10 basically comprises a bleaching head 12 and a control console or casing 14. The bleaching head 12, as will be explained hereinafter, is for the purpose of simultaneously providing heat to a multiple of teeth for bleaching, while a relatively slim, long bleaching probe 16 is provided for the purpose of activating the bleaching solution on an individual tooth. Both the bleaching head and probe provide the necessary heat for activating the bleaching solution. Clearly, the dentist performing the bleaching procedure on a patient will select the bleaching head 12 or the probe 16, depending upon the number of teeth that are being bleached, at the same time. The bleaching head 12 is preferably a plastic, basically circular shaped enclosure which, in the preferred embodiment, measures approximately 3.2 inches in diameter and about 5 inches in length. So as to provide a contemporary appearance, the bleaching head 12 actually tapers backwardly at about a 3° angle. The bleaching head 12 has an exterior cylindrical surface wall 18 and a rearwall 20.

Figure 3:
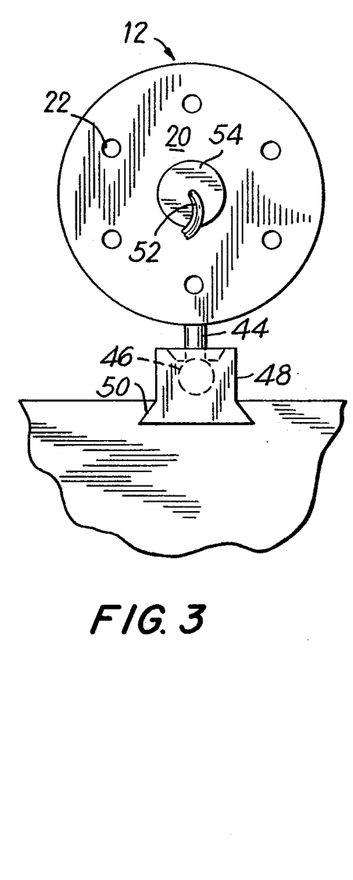
FIG. 3 is a partial rear view of the dental bleaching instrument showing the mounting of the bleaching head to the control console.

The rear wall 20 is provided with ventilation openings 22 (See FIGS. 2 and 3). A front cap 24 is provided with a plurality of radially extending vent-like openings 26 and a front central opening 28.

The bleaching head 12 preferably contains a 50 or 75 watt halogen metal reflector lamp 30. The bulb receptacle 36 is secured to the inside of surface wall 18 by support members 32 and 34. The reflector lamp 30 is screwed into bulb receptacle 36 in a conventional manner. The electrical wiring 52, for powering the bulb 30 is, of course, electrically connected to the bulb receptacle 36. As shown in FIG. 2, if a reflector is not actually incorporated into the bulb, itself, then a parabolic or curved metal reflector 38 is provided for the purpose of focusing and directing the heat energy emitted by the reflector lamp 30 so that it passes through front opening 28. The metal reflector 38 effectively prevents radiant energy from doing serious damage to the plastic enclosure of the bleaching head 12. In the preferred embodiment, a small, relatively quiet fan module 40 is located rearwardly with respect to the bulb receptacle 36. The fan module 40, when powered, moves air across the lamp 30, by first pulling air through the front intake vent-like openings 26 and expelling that air out through the rear of the bleaching head through ventilation openings 22. The fan module 40 is electrically connected to the wiring 52 for the reflector lamp 30 such that the fan will only be activated when the lamp, itself, is powered and energized. The wiring 52 passes through a strain relief mechanism 54, located in rear wall 20, and is connected to the electrical components housed within control console 14.

Also incorporated within the bleaching head 12 and, preferably, secured to the front cap 24 is a spectral filter 42 which is specifically designed to substantially reduce the glare characteristics of optical visible white light from reaching the patient. In the preferred embodiment, the spectral filter also serves to prevent all ultraviolet wavelength energy from being transmitted to the patient. The preferred embodiment fo the filter 42 blocks light transmission in the range of about 2,000 A to about 7,500 A and allows passage of infra-red energy having wavelengths of about 7,500 A and greater. Also, according to the preferred embodiment of the invention, the spectral filter 42 will allow some optically visible red light to pass in the range of about 6,500 A to 7,500 A along with some optically visible blue light in the wavelength range of about 4,500 A to about 5,000 A. Therefore, the actually emitted visible light from the reflector lamp 30, after passage through the filter 42 will appear dark red with possibly purple tones. This, facilitates the aiming and focusing of the IR wavelength of the reflector lamp directly onto the desired teeth sought to be bleached.

The front cap 24 can be provided with internal screw threads which matingly engage with external screw threads of the front portion of exterior surface wall 18, so that the front cap 24 along with the spectral filter 42 can be removed from the bleaching head 12 and the reflector lamp 30 replaced, as required and desired. Alternatively, the front cap 24 can be screwed to the main body of the bleaching head by two or three screws.

Figures 4, 5:
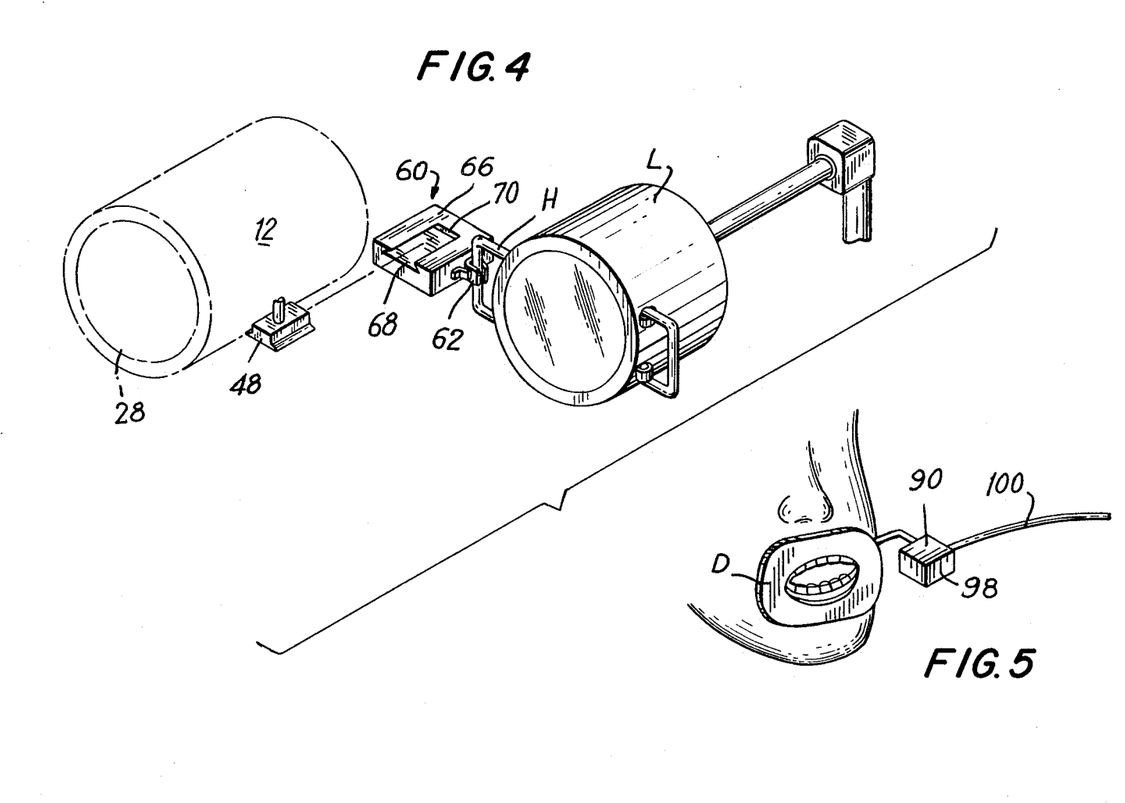
FIG. 4 shows a separate clamp element for the dental bleaching head, as secured to an existing dental operating light (partially shown) and also shows the dental bleaching head, in phantom, with its dovetail sliding block, prior to being inserted into the clamp.
FIG. 5 is a partial perspective view showing a patient during the bleaching procedure, with a rubber dam temporarily secured to the patient's mouth and with the temperature sensing means located closely adjacent to the teeth of the patient and electrically connected to the dental bleaching instrument.

A downwardly extending rod 44 is fixedly secured to the rear and bottom portion of the bleaching head 12 (See FIG. 2) and is provided with a ball and socket joint 46 at its lower most extremity. The ball and socket joint 46 allows the bleaching head 12 to be directed and aimed left and right, up and down, as desired so that the IR energy emitted by reflector lamp 30 can be precisely focused substantially perpendicularly onto the teeth sought to be bleached. The rod 44 is preferably about ⅜ of an inch in diameter. As best seen in FIGS. 2, 3, and 4, the ball and socket joint 46 is housed in a dovetail sliding block 48. A corresponding and matingly engageable dovetail sliding block receptacle 50, opened at the top and rear of the casing 14 is provided and supports the bleaching head 12 on the control console 14. The dovetail sliding block 48 of bleaching head 12 can be selectively inserted into the dovetail sliding block receptacle 50 by forward sliding and removed by relative rearward sliding. When dovetail sliding block 48 is inserted into the dovetail sliding block receptacle 50, the ball and socket joint 46 serve to provide the bleaching head 12 with significant positional adjustability which, in combination with the narrow range of wavelengths of optically visible light, emitted by the reflector lamp 30, provided by the spectral filter 42, allows the dentist to aim and focus the heat provided by the reflector lamp so that it lands precisely perpendicularly on the tooth surface or teeth sought to be bleached.

The dovetail sliding block 48 allows auxiliary or remote mounting of the bleaching head 12 with respect to control console 14. A separate clamp member 60 provides auxiliary support for the bleaching head 12, as best seen in FIG. 4. Clamp 60 includes a closed biased, spring-like holding members 62 which is adapted, preferably, to encircle and grip one of the positioning handles H of an overhead operating light L. The clamp 60 includes a block member 66 which itself is provided with a dovetail shaped receptacle 68. A rear vertical wall 70 of the dovetail shaped receptacle 68 serves to provide an abutment or stop surface for the relative rearward movement of dovetail sliding block 48, when the bleaching head 12 is desirably mounted on clamp 60. Mounting of the bleaching head onto the overhead light results in tremendous positional advantages for both the light and the patient's comfort.

The control console or casing 14 is approximately 8 inches wide, 6 inches deep and 3 inches high. It is basically an electronic type cabinet with suitable upper and rear wall vent holes (not shown) for cooling the unit, during use. The control console 14 effectively integrates the single tooth bleaching probe 16 with the multiple tooth, wide angle bleaching head 12. The control console or casing 14 has a front panel 72 where mode control and temperature selection controls, 74 and 76 preferably, in the form of turning knobs are located. Mode control knob 74 is a three positional switch which includes a central "off" position for blocking all power to the dental bleaching instrument. If the mode control knob 74 is turned counterclockwise, the bleaching head 12 will be activated while a clockwise rotation of mode control knob 74 serves to activate and provide power to the bleaching probe 16. A marker line 84 is located on the mode control knob 74 which, with demarcation lines 86 and LEDs 88, indicate to the dentist the mode of operation of the device. It should be appreciated that the control console 14 is electrically connected, through suitable wiring passing through its rear wall 89, to an ordinary electrical outlet, located in the dentist's office and providing 120 volts of alternating current, 60 Hz and 1.0 Amps.

The temperature knob control 76 is an infinitely variable or, alternatively, incrementally variable, multi-positional knob and cooperates with a series of LEDs passing through the front panel 72 of the casing to effectively control and display the actual temperature of the heat generated by the selected bleaching probe 16 or bleaching head 12. The temperature control knob 76 includes a marker 78 which is rotated to the desired demarcation line 80 corresponding to the temperature that the heat source is desirably to be operated at. The marker, along with a series of demarcation lines 80, corresponding to the temperature range desired for the bleaching procedure, allows the dentist to adjust temperature control knob 76 to a preselected and desired temperature of operation. The LEDs 82, as well as the demarcation lines 80, are labelled to reflect the temperature range of operation of the dental bleaching instrument which, in the preferred embodiment, ranges from about 120° to about 160° F. As the actual temperature of the heat generated by bleaching head 12 or probe 16, as sensed by the temperature sensing mechanism, the thermocouple, more fully explained hereinafter, reaches the indicated temperature of the demarcation lines 80, the electronics of the instrument progressively cause the LEDs to light up and remain lit until the temperature drops below the temperature of the demarcation line. Thus, the front panel 72 shows the desired or preselected temperature of operation (marker 78 and demarcation lines 80, as labelled) and, in addition, displays the actual temperature, as sensed by the temperature sensing mechanism (LEDs 82).

In one embodiment of the present invention, a temperature sensing mechanism, a temperature probe 90, is located immediately proximal to the reflector lamp 30 to measure and control the reflector lamp 30. Temperature probe 90 measures to actual temperature of the heat emitted by the reflector lamp 30. This location of the temperature probe 90, closely adjacent to the reflector lamp 30, is best shown in FIG. 2. The wiring 94 serving to connect temperature probe 90, preferably, in the form of a thermocouple, to control console 14, exits from the bleaching head 12 along with the wiring 52 coming out of the back of the bulb receptacle 36 and fan module 40. The strain relief member 54 allows passage of the wiring 52 and 94 from the bleaching head 12 through the rearwall 20 of the bleaching head. The wiring and the internal electronics of the control console are well known to those of ordinary skill in the art and are not being described in that they are conventional.

As an alternate arrangement and, indeed, the preferred embodiment of the present invention, it is contemplated that the temperature probe 90 is housed in a material mass having substantially identical thermal properties to the thermal properties of ordinary tooth structure. In this embodiment, the temperature probe 90 will be a small clip-on device (see FIG. 5) which is designed to be attached proximal to the patient's teeth or mouth. According to the embodiment shown in FIG. 5, the temperature probe 90, housed in a material mass 98, of thermal properties the same as the patient's teeth which are being treated, is clipped onto a rubber dam D which is temporarily secured, as is presently conventional, to the patients mouth and serves to prevent the caustic bleaching solution from contacting the face of the patient during the bleaching procedure. With the temperature probe 90 located proximal to the teeth and, yet, electrically connected back by wiring 100 to the control console 14, again, the actual temperature sensed by the temperature probe 90 will be reflected on the LEDs of the front panel 72. If the actual temperature sensed becomes too high compared to the selected temperature, for the particular procedure then, of course, the dentist will reduce the selected temperature of the reflector lamp 30 by turning, counterclockwise, the temperature control knob 76. Alternatively, however, if the actual temperature sensed by the temperature probe 90 and indicated on the LEDs 82 is not sufficient for the bleaching purpose desired, then the temperature control knob 76 will be rotated clockwise to increase the desired and actual temperature of the reflector lamp 30, so that the actual temperature, as sensed by the temperature probe is increased. Thus, temperature variations of the lamp heat output can be manually adjusted so that the actual output closely matches the desired output.

In a preferred embodiment of the present invention, the temperature probe 90 is electrically connected to the basic circuitry for the reflector lamp by a feedback type circuit such that the instrument is constantly monitoring the actual temperature of emitted heat and automatically adjusting the current provided to the reflector lamp so that the heat generated closely approximates, if not becomes substantially equal to, the desired preselected temperature. Housing of the thermocouple within a material mass 98 whose thermal properties approximate the thermal properties of actual tooth structure is intended to duplicate, as close as possible, the thermal absorption, reradiation or conduction properties of the very teeth which are being bleached. This, too, provides accurate data to the dentist of the temperature of the tooth structure during bleaching. It is also contemplated that, as an alternate to a material mass having thermal properties like ordinary tooth structure, the material mass could be a wholly different material so long as a mathematical temperature relationship can be established between the temperature sensed by the thermocouple in the material mass and the temperature of the patient's teeth surfaces.

As previously indicated, the temperature control knob 76 is a rotary knob and cooperates with the lines of demarcation 80 and the LEDs 82, which are labelled at about 5 degree F increments. The range provided by all of the LEDs and demarcation lines 80 will, in the preferred embodiment, extend from about 120 degrees F. to 160 degrees F., or a narrower range may be provided. The purpose of the 5 degree F increments is to provide meaningful temperature selection capabilities to the operator. It is extremely difficult to control the temperature of either the bleaching head 12 or the single tooth bleaching probe 16 to a degree of accuracy of plus or minus 1 degree F. and, therefore, displaying 1 degree increments would be extremely misleading. For this reason, the commercial practicality of the situation requires that 5 degree increments be indicated.

As mentioned, temperature indicators, in the form of high brightness LEDs 82 are located above each of the demarcation lines 80. The LEDs are small, indeed, microminiature and as the temperature of the actually sensed temperature increases, the LEDs will successively light up, i.e., sequentially, until the actual temperature sensed by the temperature probe 90 is reached. This will provide a dynamic visual indicator to the dentist as to the actual temperature status of the reflector bulb (if the probe is located near it) or the surface of the treated teeth (if the temperature probe is located near the rubber dam). It should be appreciated that the mode selection switch i.e., control knob 74, allows for the selection of either the bleaching head 12 or the single tooth bleaching probe 16. The mode selection switch also has a central position which provides an "on-off" control for the entire instrument. The switching "on" of knob 74, for either probe 16 or head 12 allows the temperature selection knob 76 to be operative. In either of the two bleaching modes, i.e., the wide bleaching head 12 or single tooth bleaching probe 16, the temperature control knob 76 and LEDs 82 will operate.

In the preferred embodiment, the reflector lamp is a high life, about 2,000 hour device. It is assumed that the system will be used at approximately 90% full power, on average. If so used, the lamp life will be extended approximately fourfold to about 8,000 total hours of available use. If the system is utilized, on average, about 4 times a day for an hour each time, then the lamp should last several years between replacements.

The front cap 24 of bleaching head 12 is capable of being removed for replacement of the reflector lamp 30 by loosening the 2 or 3 screws that fasten it to the main body or, alternatively, as previously mentioned, by providing the main body with external screw threads and the front cap 24, at its rear, with internal screw threads which matingly engage with one another. After removal of the front cap 24 the reflector lamp 30 is then free to be pulled out far enough to disconnect the electrical (twist and turn) connector and a new lamp can replace the old lamp.

The dental bleaching instrument is preferably operated at standard U.S. voltage specifications which would be 120 volts, of alternating current, 60 Hz, 1.0 amps.

In use, a dental patient is seated in the ordinary dental chair. The chair is adjusted to the comfort level of both the patient and the dentist, preferably, with the patient substantially leaning back in a relaxed position and easy access to the patient's mouth being achieved by the dentist. The teeth of the patient, i.e., those which are intended to be bleached, are then pushed through the rubber dam D which is held in place by the teeth to be bleached, by themselves and, if necessary, in addition, by additional teeth in a conventional manner. As previously mentioned, the rubber dam D serves to prevent the caustic bleaching solution from physically contacting the patient's skin during the bleaching procedure. Then, the solution, namely, peroxide or Superoxol is applied to the teeth manually, as by brushing or painting, or, alternatively, the tooth or teeth, which are desired to be bleached are first wrapped with gauze, which material is then soaked with the bleaching solution. If intra coronal dental work has been performed, then the solution is poured into a small hole in the tooth. After the teeth are prepared, the bleaching solution is ready for activation by a heat source. The dental bleaching instrument is turned "on" by first rotating mode control knob 74 from the first "off" position to either of the two "on " positions corresponding to the activating position for the bleaching probe 16 (if only an individual tooth is being bleached) or to the activating position for the bleaching head 12 (where multiple teeth are desirably being bleached simultaneously). Then, the dentist will rotate the temperature control knob 76 such that its marker 78 is aligned with the appropriate demarcation line 80 corresponding to the selected temperature of operation for activating the bleaching solution. The demarcation lines 80, of course, are labelled in 5 degree F. increments.

In the first situation where an individual tooth is to be bleached, the dentist will merely contact the tip portion of the bleaching probe 16 against either directly on the coated tooth surface or onto the soaked gauze. The bleaching probe is quite similar to a soldering iron in that it merely provides heat, by contact. The contact provided by the bleaching probe must be for a sufficient period of time of activating or "curing" the peroixde, Superoxol solution or the bleaching solution, to thereby produce desired bleaching. The bleaching probe's temperature can be simply controlled by manually turning the temperature control knob 76 to provide more or less power to the tip.

In the other situation, i.e., where the bleaching head 12 is desirably used so as to simultaneously bleach a multitude of teeth, the teeth are prepared, and then the mode control knob 74 is switched from the "off" position to the bleaching head position, by rotation of the knob in a counterclockwise direction. Then the bleaching head is aimed, facilitated by the non-filtered visible light, in the preferred embodiment, towards the teeth. The temperature sensing mechanism is located, in one embodiment, near to the bulb or, alternatively, it can be remotely located proximal to the patient's mouth by being clipped onto or otherwise secured to the rubber dam D. As previously mentioned, the thermocouple or temperature probe 90, when located near to the patient's teeth, is, preferably, secured and housed within a material mass which closely simulates and approximates the thermal properties of ordinary tooth structure. Irrespective of where the temperature sensing is performed, the LEDs 82 indicate the actual sensed temperature. The electronic circuitry of the dental bleaching instrument then serves to control the temperature of the actual heat generated by the bulb of the bleaching head, so that the temperature actually being delivered to the patient's teeth will be closely equal to the preselected and desired temperature. If the temperature actually being sensed by the thermocouple begins to creep above the preselected temperature, then the electronic circuitry, in the preferred embodiment an electrical feedback circuit is provided, will automatically decrease the power provided to the bulb. On the other hand, however, if the temperature starts to drift below the preselected temperature, the electronic circuitry will automatically increase the power to the bulb so that the actual temperature being provided by the bleaching head, as sensed by the temperature probe, is closely equal to the preselected and desired temperature. Of course, in a less complicated version, the adjustment of the actual temperature to the desired temperature is done manually by merely turing up or down the temperature control knob 76. The LEDs 82 of the instrument, will again, indicate the actual temperature sensed by the temperature probe 90. If the temperature is not closely equal to the desired temperature, the dentist can manually turn the temperature control knob 76 until favorable results are achieved. After an appropriate period of time has elapsed, the bleaching procedure is completed and the mode control knob is switched from the "probe" or "bleaching head" position to the "off" position.

The electrical circuitry of the feedback circuit provides that the temperature actually sensed by the temperature probe 90 (located closely proximal to either the reflector bulb or to the patient's mouth) precisely control the actual heat emitted by the reflector bulb. In this manner, the feedback circuitry adjusts the power delivered to the bulb so that the preselected desired temperature is approximately achieved by the actual heat generated by the bulb.

It will be appreciated that the particular description of the embodiments disclosed herein and, indeed, even the preferred embodiment are representative only of the invention and the scope to which the inventors are entitled is the scope of the claims and their legal equivalents.

We claim:

1. A dental bleaching instrument comprising
   (a) a heat generating means capable of directing heat onto at least one tooth surface for activating bleaching means thereto;
   (b) electrical power means for controlling the temperature of said heat generating means; and
   (c) temperature sensing means electrically connected to said electrical power means; said temperature sensing means including means for positioning proximal to the tooth to be bleached and yet distanced from said heat generating means for sensing the temperature of the heat generated by said heat generating means substantially close to the tooth surface after said heat has passed from said heat generating means to said tooth surface and for providing a signal means responsive to said sensed temperature.

2. A dental bleaching instrument as claimed in claim 1 wherein said signal means further comprises a temperature display means for indicating said sensed actual temperature of the heat generated by said heat generating means.

3. A dental bleaching instrument as claimed in claim 1 comprising an electrical feedback circuit means connected to said temperature sensing means and said electrical power means for adjusting said electrical power means so that the sensed temperature of the heat generated by said heat generating means is about equal to a preselected temperature.

4. A dental bleaching instrument as claimed in claim 1 wherein said temperature sensing means comprises a thermocouple embedded in a material mass of about the same or mathematically analogous thermal properties as ordinary tooth structure.

5. A dental bleaching instrument comprising
   (a) a wavelength generating means capable of generating a complete spectrum of wavelengths including IR UV and optically visible wavelengths, onto at least one tooth surface,
   (b) electrical power means for controlling the temperature of heat of said IR portion of said wavelength generating means; and
   (c) filtering means for substantially filtering the UV and all but a narrow range of optically visible wavelengths from reaching the environment immediately surrounding said tooth surface.

6. A dental bleaching instrument as claimed in claim 5, wherein the wavelength of the IR portion of said spectrum allowed to pass by said filtering means is greater than about 7500 A.

7. A dental bleaching instrument as claimed in claim 5, wherein said narrow range of optically visible light is in the range of about 6500 A–7500 A and 4500 A–5000 A.

8. A dental bleaching instrument comprising:
   (a) a heat generating means comprising a unit housing a heat source for providing and directing heat onto at least one tooth surface; and (b) an electrical power and controlling means for supplying power to and controlling the temperature of said heat provided by said heat generating means, said unit housing of said heat generating means being selectively physically disconnectable and removable from said electrical power and controlling means yet electrically connected thereto, said unit housing including means for selectively attaching and securing said unit housing, and to an accessory holding device and for adjustable location of said heat generating means proximal to the tooth of the patient to be treated.

9. A dental bleaching instrument as claimed in claim 8, wherein said heat generating means comprises a clamping means for securing the same to the overhead operatory light in a dental office.

* * * * *